| United States Patent [19] | [11] | 4,189,397 |
|---|---|---|
| Allen | [45] | Feb. 19, 1980 |

[54] STABILIZATION OF 1,1,1-TRICHLOROETHANE COMPOSITIONS AGAINST METAL-INDUCED DECOMPOSITION WITH A POLYALKYLENE GLYCOL MONOALKYL ETHER

[75] Inventor: Christopher S. Allen, Runcorn, England

[73] Assignee: Imperial Chemical Industries Limited, London, England

[21] Appl. No.: 860,948

[22] Filed: Dec. 15, 1977

[30] Foreign Application Priority Data

Dec. 24, 1976 [GB] United Kingdom ............... 54112/76

[51] Int. Cl.$^2$ .......................... C23G 5/02; C07C 17/42
[52] U.S. Cl. ..................... 252/171; 134/40; 260/652.5 R
[58] Field of Search .............. 252/171, 364; 260/652.5 R; 134/40

[56] References Cited

U.S. PATENT DOCUMENTS

| 2,371,644 | 3/1945 | Petering et al. ............... 252/171 X |
|---|---|---|
| 3,074,890 | 1/1963 | Grammer .................. 252/171 |
| 3,128,315 | 4/1964 | Hardies ................. 260/652.5 R |
| 3,269,953 | 8/1966 | Boothman ............. 260/652.5 R X |
| 3,701,627 | 10/1972 | Grunewalder .............. 252/171 X |
| 3,957,893 | 5/1976 | Beckers et al. ............. 260/652.5 R |
| 4,056,403 | 11/1977 | Cramer et al. ............. 252/171 X |

FOREIGN PATENT DOCUMENTS

| 2002284 | 7/1970 | Fed. Rep. of Germany . |
|---|---|---|
| 1936987 | 2/1971 | Fed. Rep. of Germany . |
| 6919493 | 7/1970 | Netherlands . |
| 892286 | 3/1962 | United Kingdom . |
| 930973 | 7/1963 | United Kingdom . |

*Primary Examiner*—Harris A. Pitlick
*Attorney, Agent, or Firm*—Cushman, Darby & Cushman

[57] ABSTRACT

1,1,1-trichloroethane is stabilised against metal-induced decomposition by incorporating a polyalkylene glycol monoalkyl ether.

13 Claims, No Drawings

STABILIZATION OF 1,1,1-TRICHLOROETHANE COMPOSITIONS AGAINST METAL-INDUCED DECOMPOSITION WITH A POLYALKYLENE GLYCOL MONOALKYL ETHER

This invention relates to the stabilisation of 1,1,1-trichloroethane.

In recent years there has been rapidly expanding use of 1,1,1-trichloroethane in industrial cleaning processes, particularly in the degreasing of metals. However, large scale use of 1,1,1-trichloroethane presents difficulties since in contact with reactive metals, including iron and aluminium there is attack on the solvent which leads to tar formation and evolution of large amounts of acid.

We have now found that a novel stabiliser or stabilising composition which includes the novel stabiliser is very effective in reducing metal induced decomposition of 1,1,1-trichloroethane.

According to the invention there is provided 1,1,1-trichloroethane stabilised by a polyalkylene glycol monoalkyl ether of formula

where R is an alkyl group containing 1 to 4 carbon atoms, R' is hydrogen or a methyl group and n is 2 or 3.

Preferably there is employed as stabiliser a diethylene glycol monoalkyl ether, that is, where n is 2. Specific examples of such ethers are diethylene glycol monoethyl ether and diethylene glycol monobutyl ether. A particularly useful ether is diethylene glycol monoethyl ether.

Quite small proportions by weight of the polyalkylene glycol monoalkyl ether, for example 0.01% by weight or less with reference to the solvent have some stabilising effect on 1,1,1-trichloroethane. Usually said ether is employed in amounts corresponding to 0.2% to 5%, for example, 0.2% to 2% by weight with respect to the solvent.

Other known stabilisers for 1,1,1-trichloroethane may also be associated with the novel stabiliser. For example useful results can be obtained when there are also incorporated in the 1,1,1-trichloroethane stabilising amounts of one or more of the following conventional stabilisers: organic nitrates, nitriles, nitroalkanes, epoxides, cyclic ethers, amines, alcohols, pyrrole and substituted pyrroles. Each of these known stabilisers is usually present in an amount not greater than 3% by weight of the solvent. Indeed considerably lower amounts of said conventional stabilisers can be used if desired.

In the present invention there may be provided concentrated solutions of the polyalkylene glycol monoalkyl ether in the 1,1,1-trichloroethane which contains much greater than the aforementioned 5% by weight. They may for example contain 20% to 70% by weight of said ether with reference to the solvent. By adding such concentrate to pure solvent or solvent depleted in said ether content there can be produced a 1,1,1-trichloroethane containing desired smaller amounts of said ether which can be used directly for cleaning of metals or for other purposes. Likewise concentrates may be utilised which containing not only a high proportion by weight of said ether but also suitable proportions of a conventional stabiliser or stabilisers which are hereinbefore disclosed.

The present invention includes within its scope a method of inhibiting decomposition due to presence of metals of 1,1,1-trichloroethane which comprises incorporating in said solvent said polyalkylene glycol monoalkyl ether and if desired also incorporating one or more of the conventional stabilisers as hereinbefore described.

The invention also includes a method of degreasing metal and other articles which comprises bringing the articles into contact with 1,1,1-trichloroethane stabilised by said polyalkylene glycol monoalkyl ether which solvent may, if desired, also contain conventional stabilisers.

The following Examples illustrate the invention.

EXAMPLE 1

The following procedures were carried out to determine the effect of specific glycol ethers for stabilisation of 1,1,1-trichloroethane in the presence of ferric chloride. 200 mls of unstabilised 1,1,1-trichloroethane having dissolved therein 10 ppm w/w ferric chloride were placed in each of three conical glass flasks and to each of these flasks was added a small quantity of a polyalkylene glycol monoalkyl ether The flasks were fitted with water cooled condensers and were heated under reflux until an indication of acidity was observed by means of a universal indicator paper at the top of the condenser. The time to develop acidity and the degree thereof for the contents of each flask were determined. The results are given in the table below.

The degree of acidity is expressed in terms of titre of N/50 NaOH.

TABLE 1

| | Stabiliser | Time (hrs) | Acidity |
|---|---|---|---|
| (1) | 0.1% w/w diethylene glycol monomethyl ether (methyl digol) | 70 | 2.3 |
| (2) | 0.1% w/w diethylene glycol monobutyl ether (butyl digol) | 70 | 1.4 |
| (3) | 0.5% w/w diethylene glycol monomethyl ether (methyl digol) | 93 | 0.8 |

COMPARISON

By way of comparison a procedure was carried out this time with 1,1,1-trichloroethane not containing any stabiliser. The results are indicated below

| | Stabiliser | Time (hrs) | Acidity |
|---|---|---|---|
| (4) | Nil | 1.5 | 27.7 |

EXAMPLE 2

The following procedures were carried out to determine the effect of specific polyalkylene glycol monoalkyl ethers for stabilisation of 1,1,1-trichloroethane in the presence of aluminium. 10 mls of 1,1,1-trichloroethane together with stabilisers were placed in each of two cylindrical glass vessels. A piece of aluminium 1.25 cms square was placed in each of the glass vessels and a circular scratch was made on the metal surface with a sharp steel scribe. The results are indicated hereinafter.

(a) 1,1,1-trichloroethane+3% w/w diethylene glycol monoethyl ether (ethyl digol).

There was no blackness on the scratch and no reaction took place. The aluminium test piece was still clean and the solvent was colourless after 1 hour.

(b) 1,1,1-trichloroethane+2% w/w ethyl digol+0.7% w/w nitromethane+0.5% w/w butene oxide.

The results obtained were as described in (a).

COMPARISON

By way of comparison the experiments were repeated with unstabilised 1,1,1-trichloroethane (c) and with 1,1,1-trichloroethane stabilised with materials not in accordance to the invention (d).

(c) Unstabilised 1,1,1-trichloroethane.

The scratch on the aluminium test piece immediately became completely black. A vigorous reaction with effervescence took place and discolouration occured around the scratch. After three minutes the solvent was completely black and the reaction continued unabated.

(d) 1,1,1-trichloroethane+0.7% w/w nitromethane+0.5% w/w butene oxide.

A reaction similar to that described in (c) took place which however was somewhat moderated in that initially only about 65% of the scratch became black and it was 10 minutes before the solvent became completely black.

What I claim is:

1. A stabilised solvent composition consisting essentially of 1,1,1-trichloroethane with a stabilising amount of from 0.01% to 5% by weight of a stabiliser which is a polyalkylene glycol monoalkyl ether of formula

where R is an alkyl group containing 1 to 4 carbon atoms, R' is hydrogen or a methyl group and n is 2 or 3.

2. A composition as claimed in claim 1 wherein the stabiliser is diethylene glycol monoalkyl ether.

3. A composition as claimed in claim 2 wherein the stabiliser is diethylene glycol monomethyl ether.

4. A composition as claimed in claim 2 wherein the stabiliser is diethylene glycol monoethyl ether.

5. A composition stabilised as claimed in claim 2 wherein the stabiliser is diethylene glycol monobutyl ether.

6. A composition as claimed in claim 1 wherein the stabiliser is present in an amount in the range 0.2% to 5% by weight of the solvent.

7. A composition as claimed in claim 6 wherein the range is 0.2% to 2% by weight of the solvent.

8. A composition as claimed in claim 1 in which there is also incorporated a stabilising amount of at least one additional stabiliser selected from the group consisting of organic nitrates, nitriles, nitroalkanes, epoxides, cyclic ethers, amines, alcohols, pyrrole and substituted pyrroles.

9. A composition as claimed in claim 8 in which the at least one additional stabiliser is present in an amount not greater than 3% by weight of the 1,1,1-trichloroethane.

10. A method of inhibiting decomposition of 1,1,1-trichloroethane due to the presence of metals which comprises incorporating in said 1,1,1-trichloroethane a polyalkylene glycol monoalkyl ether as described in claim 1.

11. The method of claim 10 further comprising incorporating at least one additional stabiliser selected from the group consisting of organic nitrates, nitriles, nitroalkanes, epoxides, cyclic ethers, amines, alcohols, pyrrole, and substituted pyrroles.

12. A method of degreasing metal and other articles which comprises bringing the articles into contact with the stabilised solvent composition as described in claim 11.

13. The method of claim 12 wherein said solvent composition includes at least one additional stabiliser selected from the group consisting of organic nitrates, nitriles, nitroalkanes, epoxides, cyclic ethers, amines, alcohols, pyrrole, and substituted pyrroles.

* * * * *